United States Patent [19]

DiCarlo

[11] Patent Number: 5,180,388
[45] Date of Patent: Jan. 19, 1993

[54] BONE PINNING SYSTEM

[75] Inventor: Paul DiCarlo, East Falmouth, Mass.

[73] Assignee: American Cyanamid Company, Stamford, Conn.

[21] Appl. No.: 545,398

[22] Filed: Jun. 28, 1990

[51] Int. Cl.⁵ .............................................. A61F 2/28
[52] U.S. Cl. ...................................... 623/16; 606/72; 606/80; 606/96; 606/99; 606/102; 606/104
[58] Field of Search ....................... 623/16; 606/60, 72, 606/79, 80, 86, 96, 98, 99, 102, 103, 104

[56] References Cited

U.S. PATENT DOCUMENTS

| | | | |
|---|---|---|---|
| 1,933,825 | 11/1933 | Sloan | 606/54 |
| 2,081,293 | 5/1937 | Davis | 606/66 |
| 2,251,209 | 7/1941 | Stader | 606/59 |
| 2,414,882 | 1/1947 | Longfellow | 606/73 |
| 2,500,370 | 3/1950 | McKibbin | 128/92 |
| 3,103,926 | 9/1963 | Cochran et al. | 128/92 |
| 3,739,773 | 6/1973 | Schmitt et al. | 606/77 |
| 3,842,824 | 10/1974 | Neufeld | 128/92 |
| 4,335,715 | 6/1982 | Kirkley | 606/72 |
| 4,341,206 | 7/1982 | Perrett et al. | 606/96 |
| 4,440,168 | 4/1984 | Warren | 606/102 |
| 4,450,834 | 5/1984 | Fischer | 606/96 |
| 4,450,835 | 5/1984 | Asnis et al. | 128/92 |
| 4,465,065 | 8/1984 | Gotfried | 128/92 |
| 4,719,907 | 1/1988 | Banko et al. | 606/96 |
| 4,760,844 | 8/1988 | Kyle | 606/102 |

FOREIGN PATENT DOCUMENTS

| | | |
|---|---|---|
| 0338779 | 10/1989 | European Pat. Off. . |
| 1029528 | 5/1958 | Fed. Rep. of Germany . |
| 825052 | 4/1981 | U.S.S.R. ............ 606/102 |

OTHER PUBLICATIONS

Bostman et al., "Ankle Fractures Treated Using Biodegradable Internal Fixation", Clinical Orthopaedics & Related Research, pp. 195-203, Jan., 1989.
Orthosorb Absorbable Pin Arthroscopic Kit, Surgical Technique, 1988 Johnson & Johnson Orthopaedics, Inc.

*Primary Examiner*—Randy C. Shay
*Attorney, Agent, or Firm*—Douglas E. Denninger

[57] ABSTRACT

An apparatus and method of securing fractured bones in place without the use of wires is disclosed. An absorbable bone pin is inserted in place by a cannulated applicator which is used to help drill a hole for the bone pin and accurately measure its depth. The applicator has a scaled recess in the handle which is used to measure the progress (depth) of the wire-type drill as it forms the hole. The drill has a marking or similar means on it for registration with the applicator scale. The bone pin is selected or cut to an appropriate length based on the depth of the hole and inserted in place by a push rod through the applicator guide tube. The applicator can have one or two guide tubes, and the tubes can be parallel or at angles to one another, depending on the usage desired. With a two-tube applicator, it is possible to better maintain the bone's pieces in place under compression until a bone pin is installed.

11 Claims, 2 Drawing Sheets

BONE PINNING SYSTEM

TECHNICAL FIELD

The invention relates generally to orthopedic surgery and provides a unique bone pinning system for treatment of bone fractures. In particular, the present invention relates to an improved apparatus and method for pinning and securing fractured bones together until they are healed.

BACKGROUND ART

Various methods and systems have been used to align, set and hold fractured bones together. Bone pins, screws, wires and guides of different types and styles are commonly used by surgeons to affix fractured bone pieces in place until they are healed. These bone fixation devices are typically removable or absorbable, although some are permanently installed in place.

In order to reduce trauma and recovery time, some devices and procedures have been developed which eliminate the need for making a major incision. The surgical pins or fasteners are installed into the bone with little or no prior incision. It is difficult to determine the precise depth of the pin or hole with some of these prior systems, and the end of the pin is often left exposed or protruding from the bone which can often cause discomfort or further complications.

DISCLOSURE OF INVENTION

The present invention relates to an improved surgical system and method for accurately installing and inserting bone pins to set and heal fractures. The applicator device and system allows accurate determination of the depth of the holes for the bone pins, as well as accurate placement of the pins. The pins preferably are absorbable and made of polyglycolic acid. They are selected or cut to a predetermined length prior to insertion and do not protrude from the bone or skin.

The applicator device has one or two guide tubes attached to a handle. A wire-type drill inserted through the guide tube is used to drill holes in the bone for the pins. One or more markings on the drill are matched or calibrated with a scale on a recess in the handle for accurate determination of the movement of the drill and thus the depth of each hole. Bone pins of appropriate diameters are selected and cut to the precise depth of the holes. The pins are placed in the applicator device which is used as an insertion guide. A plunger or push rod is used to forcibly push the bone pins into the holes. The pins securely hold the fractured bone pieces in place until they become fused together.

Where a single tube application device is utilized, the procedure is repeated several times until the desired number of pins are installed in place. Where a two tube application device is utilized, a guide wire, drill or bone pin positioned in one hole can be used to keep the fractured bone pieces set and held together while a second hole is formed. This prevents any disturbance of the positioning of the bones due to withdrawal of the drill or guide wire. In a two or multiple tube application, it is possible to angle or skew the orientations of the tubes in order to allow the drills and pins to "wedge" the bone pieces together and thus aid in holding them in place.

In accordance with the present invention, it is a basic object to provide an improved bone pinning system to help hold fractured bones in place until they are healed. Another object of the invention is to provide a bone pinning system which accurately and precisely determines the depth of the drilled hole and thus allows accurate selection of the appropriate pin.

It is also an object of the invention to provide a relatively simple and easy to use bone pinning system which utilizes absorbable pins and prevents them from protruding outside the bone or skin. It is a still further object of the present invention to provide a bone pinning applicator which allows the fractured bone pieces to be held securely in position during the bone pinning drilling and installation procedure.

Other advantages and objects of the invention will become more apparent from the description of the drawings and preferred embodiments as set forth in the remainder of the specification.

BEST MODE FOR CARRYING OUT THE INVENTION

Figure 1:
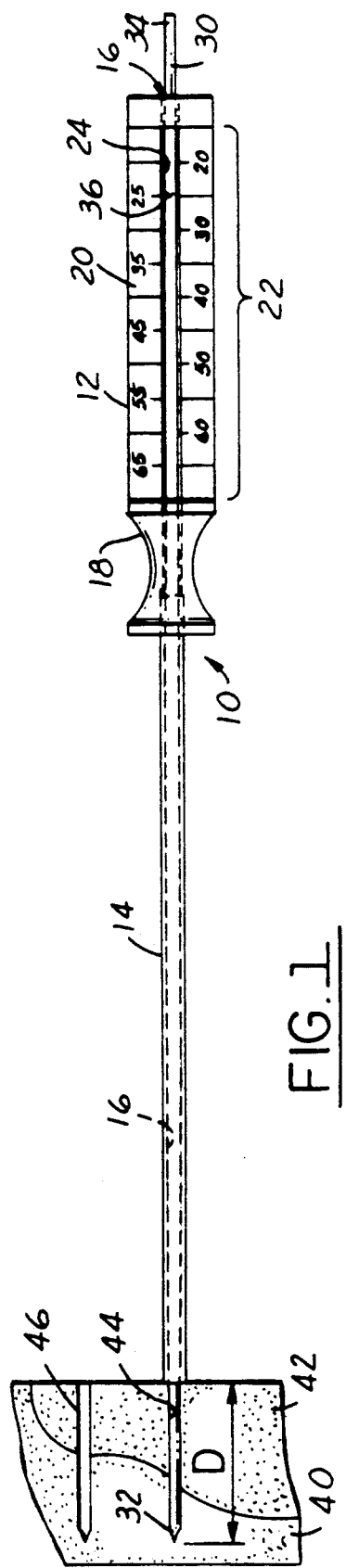
FIG. 1 illustrates the present invention being used to drill a hole for a bone pin.
Figure 2:
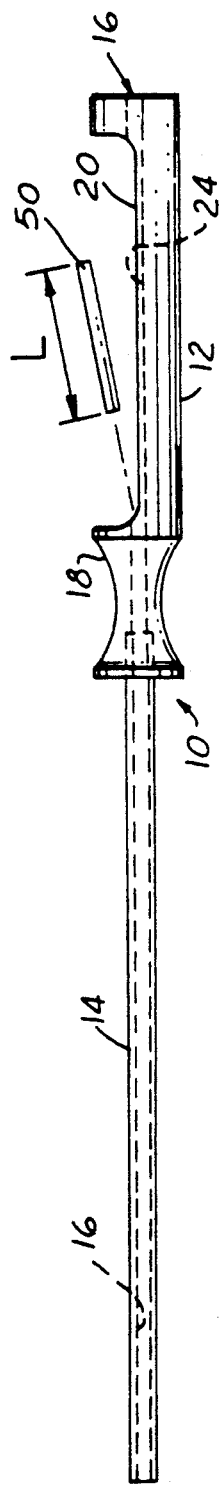
FIG. 2 is a side view of the inventive applicator device and showing a bone pin for subsequent insertion into a bone.
Figure 3:
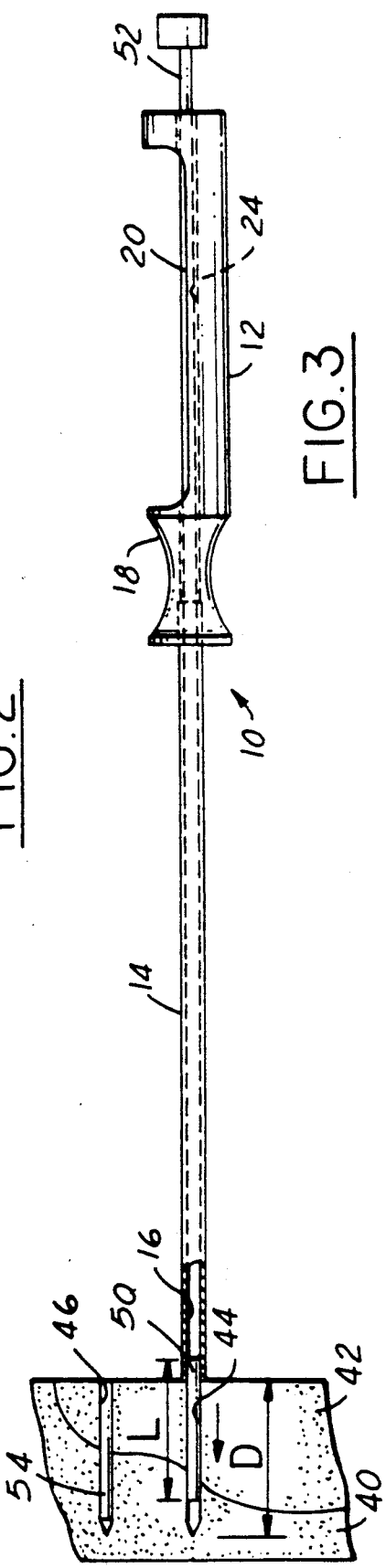
FIG. 3 illustrates the insertion of a bone pin into a drilled hole in a fractured bone.

FIGS. 1-3 illustrate a single tube applicator device and its use in accordance with the present invention. The applicator device is generally designated by the numeral 10. It has a handle 12 and a tube 14. The applicator device 10 is cannulated, that is, it has a channel or opening 16 extending throughout its length.

The handle 12 is preferably made of an autoclavable metal (e.g. aluminum) or plastic, a disposable metal or plastic or any equivalent materials. The tube 14 is preferably made from a metal material (e.g. stainless steel) which has sufficient strength to meet the projected uses of the device 10 and also is autoclavable.

The handle is generally circular in cross-section with a curved portion 18 at one end to aid the surgeon in manually holding and maneuvering it into position. A recess portion 20 is formed in the handle and has a scale or calibrated markings 22 on it. The markings 22 are preferably in millimeters, but they can be provided in thousandths of an inch or any convenient or appropriate scale for use by the surgeon.

The recess 20 is recessed to a depth where it intersects the opening 16 forming an open channel 24 in the handle.

The opening 16 has a cross-sectional size to allow a wire-type drill 30 (or guide wire) to be freely insertable and slidable within it. The drill 30 has a pointed tip 32 at one end. The opposite end 34 of the drill sufficiently protrudes beyond the end of the applicator device 10 and is adapted to be held in a mechanical or electrical drill (not shown).

The wire drill 30 has one or more marks 36 on it which are used to indicate its position relative to the scale 22. It is understood that any type of visible marking or fixed indication on the drill can be utilized to indicate its relative position relative to the handle. For example, the drill could have a colored ring around it at a certain point, or be provided in multiple colors and have a color separation line at a certain point. It is also understood in accordance with the present invention that the scale means could be provided on the drill and a marking of some type be positioned on the handle. It is also possible to use a guide wire in holding the bone pieces together temporarily after the hole is formed.

When the application device 10 is utilized, it is positioned against the skin or bone adjacent the fractured bone pieces 40 and 42. A wire drill 30 is then inserted in the central aperture 16 and used to drill a hole 44 in the two bone pieces. (A previously drilled hole 46 is also shown in FIG. 1.) The depth D of the hole 44 is accurately determined by the movement of the mark 36 on the drill relative to the markings on the scale 22. In this manner, the surgeon can drill each bone fixation pin hole to a precise and/or desired depth.

Once the hole is formed to the prescribed depth D, the bone pin 50 is selected and cut to a length L which matches the depth D. If a series of bone pins are provided or available of different lengths, it is possible to simply select one of an appropriate length. (If pins of a certain length are provided initially, then it may be possible depending on the circumstances for the surgeon to drill the holes to a depth to match the bone pins.) If desired, the length L can be any length less than the depth D of the hole so that the pin 50 will not protrude beyond the entrance of the hole 44, and/or will promote immediate bone growth at the entrance to the hole 44.

The actuator device 10 can be provided in a kit form with a plurality of bone pins of different lengths and cross-sectional sizes. A pin is selected which matches the diameter of the drill 30 which is used to drill the hole 44. The bone pin 50 is selected of the appropriate length L or cut to a desired length for use in the surgical procedure.

As mentioned earlier, the bone pins are preferably made of an absorbable material, such as polyglycolic acid (PGA). Absorbable surgical structural elements made of PGA are disclosed in U.S. Pat. No. 3,739,773. It is, of course, possible with the present invention to also use bone pins made of metal or another suitable material.

The bone pins preferably are on the order of 1-4.5 mm in diameter, and the actuator device (handle and tube) is preferably about 6-12 inches in length.

Once the bone pin 50 is selected of the appropriate size and length, it is placed in the opening 16 in the handle 12 (as shown in FIG. 2). Due to the recess 20, the pin can be inserted in the tubular opening 16 at the position shown in FIG. 2. The pin 50 is then pushed through the handle 12 and hollow tube 14 into the hole 44 by means of an elongated plunger or push rod 52. This is shown in FIG. 3. The forcing of the pin 50 into the drilled hole 44 compresses the bone pieces 40 and 42 together. The pin 50 holds the fractured pieces securely together until they are fused in place and healed. In FIG. 3, a bone pin 54 is shown which has been previously installed in place in second hole 46.

After the bone pins 50, 54, etc. are installed in place, the push rod 52 and applicator device 10 are removed and the wound is closed or dressed as needed. The precise number of bone pins required to securely hold the bone pieces together and heal the fracture is determined by the type and severity of the fracture and the desires of the surgeon. Typically two or more bone pins are utilized in most situations.

Figure 4:
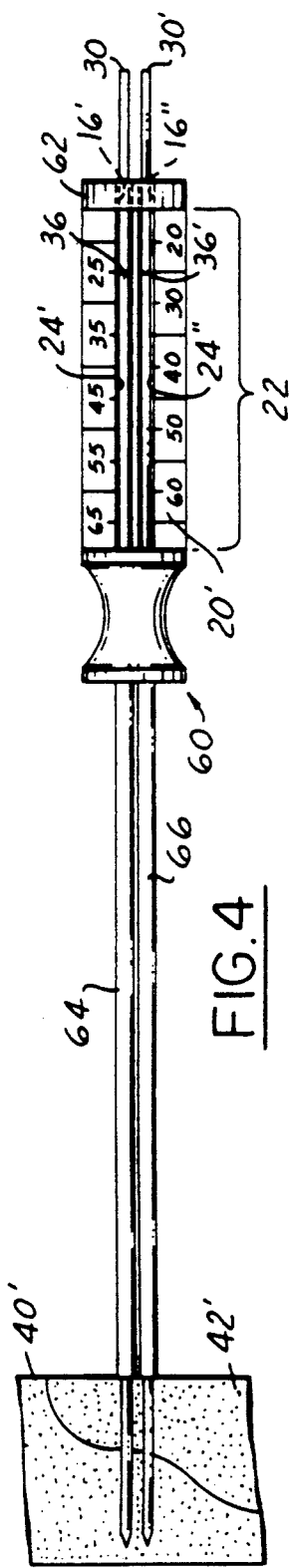
FIG. 4 illustrates a double tube applicator device in accordance with the present invention.

An alternate embodiment of the bone pin applicator device is shown in FIG. 4. The device 60 has a handle portion 62 and a pair of parallel hollow tubes 64 and 66. With the exception of two tubes and their associated openings 16', 16" and channels 24' and 24", the device 60 is essentially the same as the device 10 described with reference to FIGS. 1-3. The device 60 is also used in substantially the same manner as device 10 to insert absorbable bone pins in place to hold fractured bone pieces 40' and 42' together.

A pair of wire-type drills 30 and 30' are used to drill the holes in the bone pieces for the bone pins. For this purpose the device 60 is used as a drill guide in the same manner as described above with reference to FIGS. 1-3. Markings 36 and 36, on the drills are used to determine the depths of the drilled holes relative to the calibrated scale 22 on the handle 62 of the device 60. The scale 22 is positioned in recess 20'.

The device 60 allows the surgeon to install two bone pins in the fractured bone pieces in a quick and simple manner. The device also allows the surgeon to retain one drill or guide wire in place in the bone through one of the tubes 64 or 66 while a bone pin is installed through the other tube. This causes the bone pieces 40' and 42' to be retained securely set and affixed in place by compression until the first bone pin is installed in place.

Figure 5:
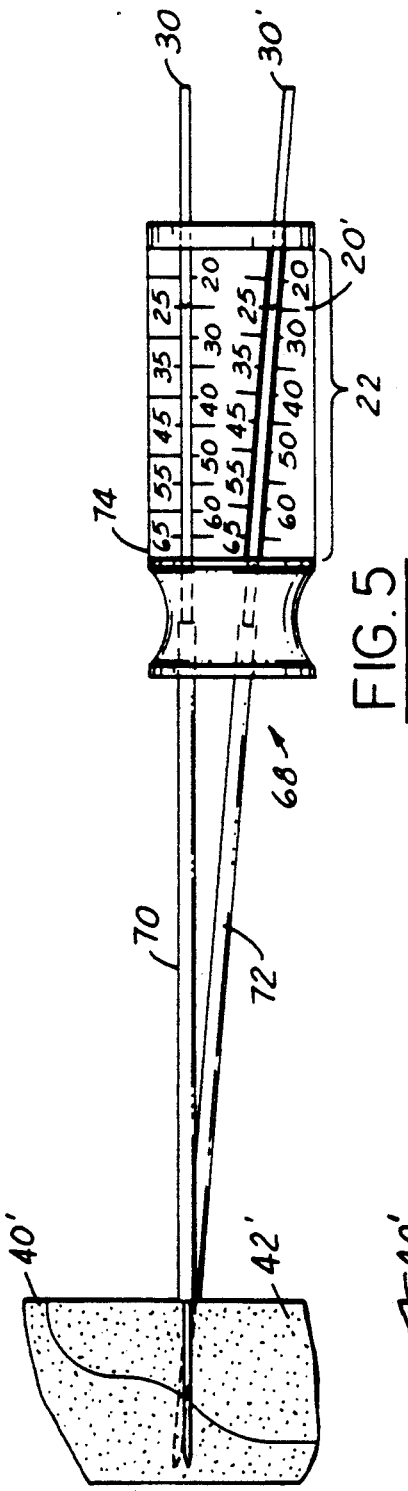
FIG. 5 illustrates an embodiment of a double tube applicator device with angled or skewed guide tubes.
Figure 6:
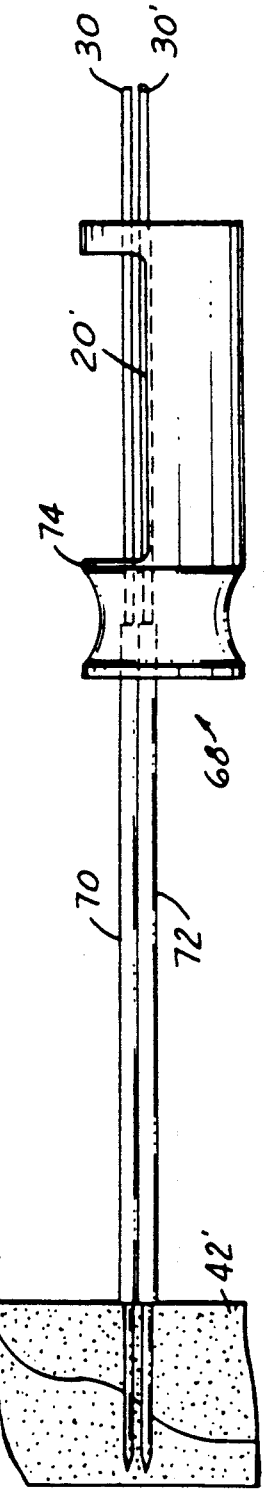
FIG. 6 is a side view of the applicator device as shown in FIG. 5.

FIGS. 5 and 6 disclose another two-tube embodiment 68 of the invention. In this alternate embodiment, the two tubes 70 and 72 are positioned at an angle or in a skewed relationship relative to one another. The tubes 70 and 72 are connected to a handle 74 which, similar to handles 12 and 62, has a recessed portion 20' and one or more calibrated scales 22. As shown in FIG. 5, it is preferable to provide two separate scales on this embodiment, one for each of the angled tubes.

The actuator device 68 is used in the same manner and for the same purpose as the devices 10 and 60 described above. The skewed insertion tubes 70 and 72 allow the wire-type drills, guide wires and subsequently installed bone pins to act to "wedge" the fractured bone pieces 40' and 42' together and help hold them securely in place until they are healed.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

I claim:

1. A method of repairing fractured bones utilizing an applicator device, drill means, plunger means and at least one bone pin means, said applicator device having a handle member defining a lateral recess and at least one tube means, said drill means having first mark means thereon and said handle member having second mark means thereon wherein at least one of the mark means is a scale, said method comprising the steps of:
   drilling a hole in said fractured bones utilizing said applicator device to guide said drill means;
   determining the depth of said hole by aligning said first mark means and said second mark means while said drill means is extending through said applicator device;

selecting said bone pin means in accordance with the determined depth of said hole prior to insertion of said bone pin means in said hole and prior to placement of said bone pin means into said applicator device; and inserting said pin means in said hole utilizing said applicator device and said plunger means by inserting said pin means into said lateral recess and then pushing against said pin means with said plunger means.

2. A method for holding two bone members together with at least one bone pin and utilizing a wire drill with first marking means thereon, and a cannulated applicator device having a handle and at least one insertion tube, said applicator device having second marking means thereon, the method comprising the steps of (a) placing the applicator device adjacent one of the bone members;

(b) drilling a first hole in the two bone members with the wire drill positioned in said applicator device;

(c) measuring the depth of the hole by comparing the first marking means on the wire drill with the second marking means on the applicator device while the wire drill is in the applicator device;

(d) removing said wire drill leaving said applicator device in place;

(e) selecting a bone pin of a desired length corresponding to such measured depth; and (f) inserting said bone pin in said hole by placing said bone pin into a lateral recess in the handle of said applicator device proximal to the insertion tube, and driving said bone pin through the insertion tube and into said hole.

3. The method as set forth in claim 2 wherein a plunger member is used to insert the bone pin into said hole by driving said bone pin through the insertion tube.

4. The method of claim 2 wherein said applicator device has two insertion tubes attached to said handle and the method further comprises the steps of (g) drilling a second hole in the two members with said wire drill being positioned in the second insertion tube;

(h) measuring the depth of the second hole using the graduated markings on the wire drill and applicator device;

(i) removing said wire drill;

(j) selecting a second bone pin of a desired length corresponding to the measured depth of the second hole; and (k) inserting said second bone pin into said second hole through said applicator device.

5. The method of claim 4 wherein said two insertion tubes are situated in a non-parallel orientation relative to one another, thereby installing bone pins in a non-parallel relation to one another.

6. The method of claim 2 wherein said step of selecting a bone pin of desired length comprises reducing a longer bone pin to the desired length prior to inserting of said bone pin in said hole.

7. An applicator device for use in inserting bone pins of a preselected length into holes formed in bone members, said applicator device comprising an elongated hollow handle member having a first passageway along its length, and an elongated hollow tubular member attached to said handle; said tubular member having a second, enclosed passageway along its length in axial alignment with said first passageway in said handle;

said handle member having a lateral recessed portion thereon intersecting said first passageway, and having a width at least as great as the diameter of said first passageway; and said recessed portion having graduated markings thereon for use in measuring the advancement of members through the first and second passageways.

8. The applicator device as set forth in claim 7 wherein said recessed portion comprises approximately one-half of said handle member in depth and has an elongated flat portion extending at least one-half the length of said handle member where said graduated markings are positioned.

9. The applicator device as set forth in claim 8 wherein said first and second passageways receive a drill means having a proximal end and calibration means carried by said drill means distal to said proximal end, said graduated markings on said recessed portion and said calibration means of the drill means being alignable to enable drilling of a hole of predetermined depth in the bone members.

10. An installation kit for installing a bone pin of a desired length into a bone, said installation kit comprising:

drill means having a proximal end and first mark means thereon distal to said proximal end;

an applicator device having handle means with a conduit therethrough for receiving the drill means, said handle means having second marks thereon for alignment with said first mark means to measure the movement of said drill means relative to said second mark means;

said applicator device further including a hollow member having a distal opening defined by a distal end positionable against the bone and a proximal opening defined by a proximal end connected with said handle means, said hollow member defining an enclosed passagway extending between said proximal opening and said distal opening;

plunger means being dimensioned to fit within said conduit of said handle means and said passageway of said hollow means to install said bone pin in said bone; and wherein the measured movement of said drill means relative to said applicator device may be used to establish the desired length of said bone pin.

11. The installation kit of claim 10 wherein said handle means further includes a laterally opening recess in communication with said conduit and sized to receive said bone pin when inserted lengthwise into said recess.

* * * * *